US010491789B2

(12) United States Patent
Shen et al.

(10) Patent No.: US 10,491,789 B2
(45) Date of Patent: Nov. 26, 2019

(54) MULTI-LIGHT APPARATUS AND METHOD FOR IMAGING A SUBJECT

(71) Applicant: KONINKLIJKE PHILIPS N.V., Eindhoven (NL)

(72) Inventors: Yu Shen, Shenzhen (CN); Gao Qin Li, Shenzhen (CN); Xiao Ming Liang, Shenzhen (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 652 days.

(21) Appl. No.: 14/889,153

(22) PCT Filed: May 29, 2014

(86) PCT No.: PCT/IB2014/061805
§ 371 (c)(1),
(2) Date: Nov. 5, 2015

(87) PCT Pub. No.: WO2014/195832
PCT Pub. Date: Dec. 11, 2014

(65) Prior Publication Data
US 2016/0080620 A1    Mar. 17, 2016

(30) Foreign Application Priority Data

Jun. 6, 2013 (WO) ................ PCT/CN2013/076870

(51) Int. Cl.
*A61B 1/00* (2006.01)
*H04N 5/225* (2006.01)
(Continued)

(52) U.S. Cl.
CPC ....... *H04N 5/2256* (2013.01); *A61B 1/00006* (2013.01); *A61B 1/05* (2013.01);
(Continued)

(58) Field of Classification Search
CPC ....... A61B 1/00006; A61B 1/05; A61B 1/051; A61B 1/0607; A61B 1/0676; A61B 1/303; H04N 5/2252; H04N 5/2256
(Continued)

(56) References Cited

U.S. PATENT DOCUMENTS 6,260,994 B1 * 7/2001 Matsumoto ............... G01J 3/02
362/574
6,533,722 B2 * 3/2003 Nakashima ............... A61B 1/05
600/129
(Continued)

FOREIGN PATENT DOCUMENTS

JP      S57173826    10/1982
JP      2000089305    3/2000
(Continued)

*Primary Examiner* — Timothy J Neal (57) ABSTRACT

The present invention provides apparatus and method for imaging a subject in clinical examination. An apparatus for imaging a subject, comprising: a plurality of light sources (20) for illuminating a region of interest within the subject, at least a portion of the light sources (20) being divided into groups and being actuated group by group, each actuated group of the light sources (20) providing an illumination flash with a predetermined duration, and different groups of the light sources (20) illuminating the region of interest at different angles; and a light detector (40) for receiving light reflected by the subject to form a frame of image for the region of interest per imaging period of the light detector (40), and the predetermined duration of the illumination flash being shorter than the imaging period, enough to enable different groups of the light sources to illuminate the region of interest per imaging period at different times within the imaging period. According to the apparatus, glint in images of the region of interest is reduced in real-time.

11 Claims, 4 Drawing Sheets

(51) Int. Cl.
*A61B 1/05* (2006.01)
*A61B 1/06* (2006.01)
*A61B 1/303* (2006.01)

(52) U.S. Cl.
CPC ............ *A61B 1/051* (2013.01); *A61B 1/0607* (2013.01); *A61B 1/0676* (2013.01); *A61B 1/303* (2013.01); *H04N 5/2252* (2013.01)

(58) Field of Classification Search
USPC ................................. 600/109, 178, 180, 135
See application file for complete search history.

(56) References Cited

U.S. PATENT DOCUMENTS

| | | | |
|---|---|---|---|
| 7,433,589 B2 * | 10/2008 | Odaka .................... | G03B 15/05 396/155 |
| 2003/0117491 A1 | 6/2003 | Avni et al. | |
| 2003/0156430 A1 * | 8/2003 | Ota ...................... | A61B 1/0669 362/574 |
| 2003/0191368 A1 * | 10/2003 | Wang .................. | A61B 1/00009 600/160 |
| 2005/0213957 A1 | 9/2005 | Tokunaga | |
| 2006/0171693 A1 * | 8/2006 | Todd .................. | A61B 1/00029 396/17 |
| 2006/0184039 A1 * | 8/2006 | Avni ...................... | A61B 1/041 600/476 |
| 2006/0184040 A1 | 8/2006 | Kurtis et al. | |
| 2006/0184043 A1 | 8/2006 | Tromberg et al. | |
| 2006/0215406 A1 | 9/2006 | Thrailkill | |
| 2008/0071144 A1 * | 3/2008 | Fein .................... | A61B 1/00167 600/178 |
| 2009/0149713 A1 * | 6/2009 | Niida ...................... | A61B 1/042 600/167 |
| 2010/0026785 A1 | 2/2010 | Soto-Thompson | |
| 2011/0032383 A1 * | 2/2011 | Imade .................. | A61B 1/0669 348/229.1 |
| 2011/0092772 A1 * | 4/2011 | Weber .................. | A61B 1/0008 600/178 |
| 2011/0184243 A1 * | 7/2011 | Wright .................. | A61B 1/0638 600/180 |
| 2013/0053642 A1 * | 2/2013 | Mizuyoshi .......... | A61B 1/00006 600/109 |
| 2014/0052004 A1 * | 2/2014 | D'Alfonso ........... | A61B 1/0669 600/476 |
| 2014/0240468 A1 * | 8/2014 | Feke ..................... | A61B 1/0638 348/47 |
| 2014/0354788 A1 * | 12/2014 | Yano ..................... | A61B 1/043 348/68 |

FOREIGN PATENT DOCUMENTS

| | | | | |
|---|---|---|---|---|
| JP | 2003161987 | 6/2003 | | |
| JP | 2005221856 | 8/2005 | | |
| JP | 2010128159 | 6/2010 | | |
| WO | 2011/146007 | 11/2011 | | |
| WO | WO2013049264 A1 * | 4/2013 | ............... | A61B 1/05 |

* cited by examiner

MULTI-LIGHT APPARATUS AND METHOD FOR IMAGING A SUBJECT

CROSS REFERENCE TO RELATED APPLICATIONS

This application is a national filing of PCT application Serial No. PCT/IB2014/061805, filed May 29, 2014, which claims the benefit of Chinese application serial no. PCT/CN2013/076870 filed Jun. 6, 2013, which is incorporated herein by reference.

FIELD OF THE INVENTION

The present disclosure relates generally to imaging, and more specifically to techniques for medical imaging for use in performing clinical examinations.

BACKGROUND OF THE INVENTION

Cervical cancer is one of the most common cancers in women worldwide. Since invasive disease is preceded by pre-malignant Cervical Intraepithelial Neoplasia (CIN), if detected early and treated adequately, cervical cancer can be universally prevented. For this reason, early detection of cancerous and precancerous lesions is particularly important at preventing the progression of the disease.

Colposcopy involves visually inspecting the cervix of patients who have some prior indication of abnormality. The procedure is conventionally performed by using a colposcope. The colposcope typically comprises a light source to illuminate a region of interest within a subject, e.g., the cervix of a patient, and an image sensor (e.g. a Charge-Coupled Device detector, i.e. CCD detector) to acquire an image of the region of interest. The acquired image will be provided to a clinician. Such colposcopic examination can be used by the clinician to identify and rank the severity of lesions, and thus a biopsy sampling of cervical tissue representing the highest-grade abnormality, may be taken, if necessary.

In order to reliably assess colposcopic features, the imagery must be of high visual quality. One factor leading to poor cervical imagery is specular reflection (i.e. glint). Usually, glint is undesirable because it effectively eliminates color information in an image (the color information can represent tissue structure and can be important in detecting cancer precursors). Reducing the amount of glint in an image is helpful in producing high-quality images for diagnostic purposes.

SUMMARY OF THE INVENTION

It would be desirable to provide a colposcope or other medical instrument to efficiently produce high-quality images that preserves image clarity while suppressing glint.

Briefly, a light source provides an illumination flash towards a region of interest within a subject, e.g., the cervix of a patient. It is the inventor of the present invention who first realized that the glint can be effectively reduced by controlling the duration of the illumination flash and an imaging period of a light detector. In particular, if the duration of the illumination flash is much shorter than the imaging period of a light detector (e.g. exposure time of a CCD detector), i.e. enough to enable different light sources to separately provide the illumination flash towards the region of interest at different angles, the light detector, within the imaging period, can receive a mix of reflected lights originating from the different light sources. Since the different light sources illuminate the subject at different angles, the glint can be effectively reduced in a frame of image that is formed on the basis of the mix of the reflected lights.

Techniques for reducing glint in images of a region of interest within one subject (e.g. cervix) are described herein.

In an aspect, the invention provides an apparatus (100, 200, 300) for imaging a subject, comprising: a plurality of light sources (20) for illuminating a region of interest within the subject, at least a portion of the light sources (20) being divided into groups and being actuated group by group, each actuated group of the light sources (20) providing an illumination flash with a predetermined duration, and different groups of the light sources (20) illuminating the region of interest at different angles; and a light detector (40) for receiving light reflected by the subject to form a frame of image for the region of interest per imaging period of the light detector (40), and the predetermined duration of the illumination flash being shorter than the imaging period, enough to enable different groups of the light sources to illuminate the region of interest per imaging period at different times within the imaging period.

In another aspect, the invention provides a method of imaging a subject, comprising: illuminating a region of interest within the subject by a plurality of light sources (20), at least a portion of the light sources (20) being divided into groups and being actuated group by group, each actuated group of the light sources (20) providing an illumination flash with a predetermined duration, and different groups of the light sources (20) illuminating the region of interest at different angles; and receiving light by a light detector (40) to form a frame of image for the region of interest per imaging period of the light detector (40), the light being reflected by the subject, and the predetermined duration of the illumination flash being shorter than the imaging period, enough to enable different groups of the light sources to illuminate the region of interest per imaging period at different times within the imaging period.

The results of experiments show that, according to techniques described herein, glint in images of a region of interest within a subject (such as organs or tissue) can be reduced in real-time, thereby enhancing the visualization of diagnostically relevant features within the subject.

Various aspects and features of the disclosure are described in further detail below. And other objects and advantages of the present invention will become more apparent and will be easily understood with reference to the description made in combination with the accompanying drawings.

DESCRIPTION OF THE DRAWINGS

The present disclosure will be described and explained in more detail hereinafter in combination with solutions and with reference to the drawings, wherein.

The same reference signs in the figures indicate similar or corresponding features and/or functionalities.

DETAILED DESCRIPTION

The present invention will be described with respect to particular solutions and with reference to certain drawings, but the invention is not limited thereto but only by the claims. The drawings described are only schematic and are non-limiting. In the drawings, the size of some of the elements may be exaggerated and not drawn to scale for illustrative purposes.

Figure 1:
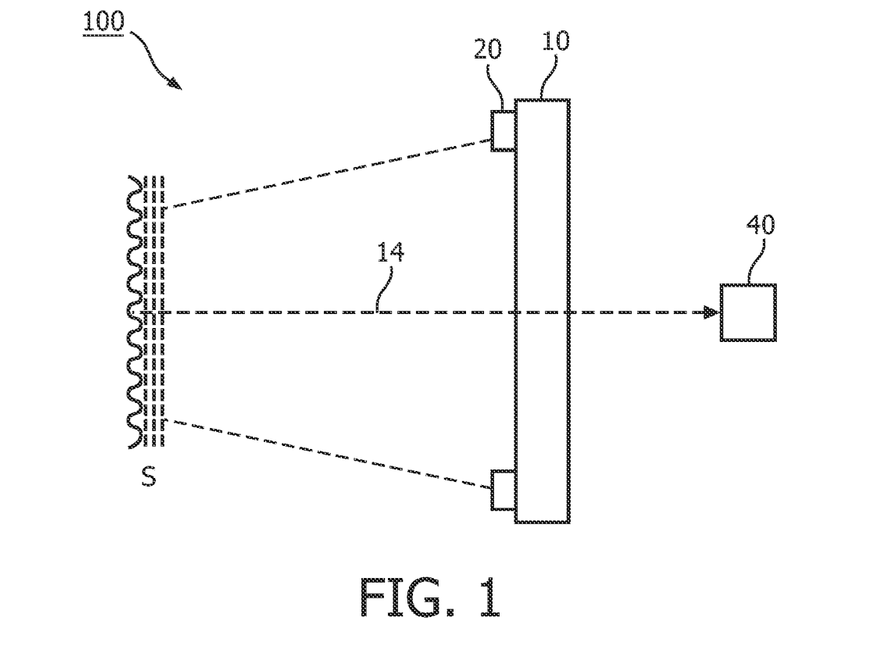
FIG. 1 is a schematic diagram of one design of an apparatus according to the teachings of the present invention.

FIG. 1 shows a schematic diagram of one design of an apparatus, indicated by reference 100, according to the teachings of the present invention. Apparatus 100 comprises a carrier 10, a plurality of light sources 20 arranged on carrier 10. Each one of the light sources 20 can be actuated to provide an illumination light at a region of interest S within a subject, in this example, an area of the cervix within a patient's body. When the illumination light interacts with the region of interest, the light is reflected by the subject. Apparatus 100 further comprises a light detector 40 for receiving the light reflected by the subject to image the region of interest. Light detector 40 can be, for example, a black and white CCD detector or a color CCD detector for providing pictures of the region of interest.

Figure 2:
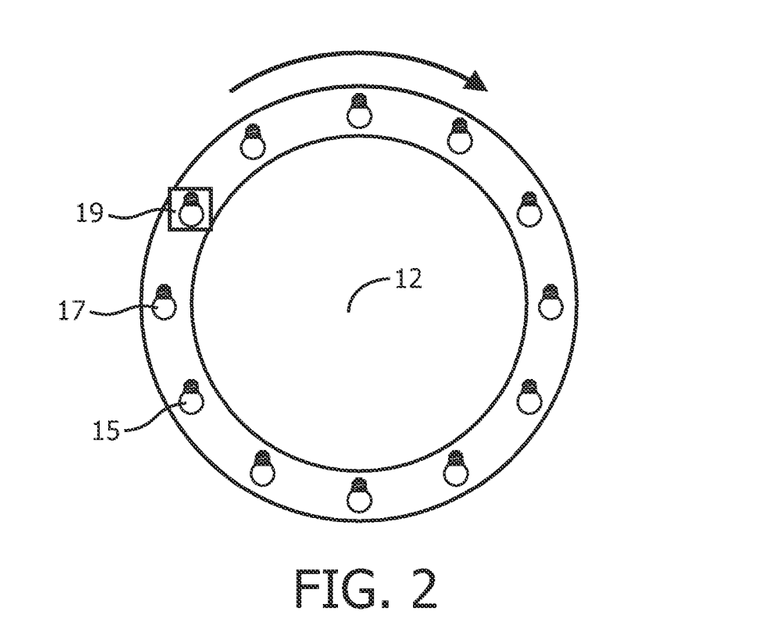
FIG. 2 is a conceptual front view of light sources according to the teachings of the present invention.

In one design, carrier 10 is a circular board. In a preferred design, as shown in FIG. 2, light sources 20 are equiangularly arranged on carrier 10 so as to surround an access opening 12 of carrier 10. In a preferred design, access opening 12 is circular in shape, wherein a central axis 14 of access opening 12 is coincident with an optical axis for viewing the region of interest. Each actuated light source, e.g. light source 19, can be controlled to emit a flash of illumination light (i.e. illumination flash) incident on the region of interest S. If the duration of the illumination flash is much shorter than an imaging period of light detector 40, then light detector 40, within the imaging period, can receive reflected lights caused by different actuated light sources. In one example design, light detector 40 is a CCD detector and the imaging period is exposure time (i.e. shutter speed) of light detector 40. The reflected lights received by light detector 40 per imaging period are used to form one frame of image for the region of interest. Since the actuated light sources are located at different positions on the circular board, the illumination flashes emitted from different light sources are directed at different angles towards the region of interest. Accordingly, glint in the frame of image is reduced effectively. That is, as light detector 40, within the imaging period, can receive a mix of reflected lights originating from different light sources 20 that illuminate the subject at different angles, the glint can be effectively suppressed in the frame of image that is formed based on the mix of reflected lights.

In a preferred design, during the imaging period, every light source is actuated once and all light sources 20 contribute to the mix of reflected lights for forming one frame of image. In another example design, during the imaging period, some light sources 20 are actuated to provide illumination light and other light sources 20 are not actuated; thus, only the actuated light sources 20 contribute to the mix of reflected lights for forming one frame of image. In another example design, during the imaging period, all light sources 20 are actuated once but some of the light sources 20 are actuated additionally, e.g. actuated twice, according to a predetermined sequence; thus, all actuated light sources 20, i.e. each time they are actuated, make a contribution to the mix of reflected lights for forming one frame of image.

In one design, light sources 20 are LEDs (Light Emitting Diodes). The use of LEDs offers several benefits. One benefit is that LEDs are driven by drive currents, thus the actuation of an individual LED or a combination of LEDs can be realized easily. A drive circuit (not shown) for supplying the drive currents to the LEDs can be disposed on carrier 10, e.g. formed integrally on carrier 10 in accordance with a preferred design. A first controller is coupled to the drive circuit via a wired or wireless connection. The first controller provides a first control signal to the drive circuit for enabling the drive circuit to actuate the LEDs. The first controller may be disposed on carrier 10 or, alternatively, may be disposed separate from carrier 10.

Another benefit of using LEDs as light sources 20 resides in that the duration of LED illumination flashes (i.e. flash duration of LEDs) can be set to be very short by controlling the drive currents applied to the LEDs. For example, a predetermined LED flash duration can be set within the range from 10 ns (nanosecond) to 100 ns. However, the imaging period of a light detector, e.g. the exposure time of a CCD detector, is usually set to be one of $\frac{1}{1}$ s (second), $\frac{1}{2}$ s, $\frac{1}{6}$ s, $\frac{1}{25}$ s, $\frac{1}{50}$ s, $\frac{1}{75}$ s, $\frac{1}{100}$ s ... $\frac{1}{10,000}$ s (e.g. SONY FCB-EX series provides 25 levels in total). It is known that is (second)=1,000,000,000 ns (nanosecond). Therefore, if LEDs are used as light sources 20, the flash duration of each LED could be much shorter than the exposure time of a CCD detector, enough to enable different actuated LEDs, directed at different angles to the region of interest, to illuminate the subject within the exposure time of CCD. A second controller provides a second control signal to the drive circuit for enabling the drive circuit to actuate the LEDs. The second controller is coupled to the drive circuit via a wired or wireless connection. The second controller may be disposed on carrier 10 or, alternatively, may be disposed separate from carrier 10.

Further, the flash duration of each LED can be adjusted by controlling the drive currents applied to the LEDs. The second controller can be used to provide a control signal to the drive circuit for adjusting the flash duration of the LEDs.

The first controller and the second controller can be individual elements or one assembly which can provide one or more control signals corresponding to the functions of the first control signal and/or the second control signal. In one example, the assembly is realized by a memory plus a processor, wherein the processor implements a software program stored in the memory to provide the one or more control signals.

The LEDs are preferably high intensity LEDs (e.g., 1-5 watt) as a result of higher fluxes and luminous densities than low intensity LEDs. Since the high intensity LEDs draw more current, they produce much more heat than low intensity LEDs. Carrier 10 is preferably made of a thermally well-conducting material such as copper. The LEDs have heat sinks which are in intimate thermal contact with carrier 10. In addition, carrier 10 may be provided with a plurality of cooling fins (not shown) to improve thermal conduction and dissipation.

Figure 3:
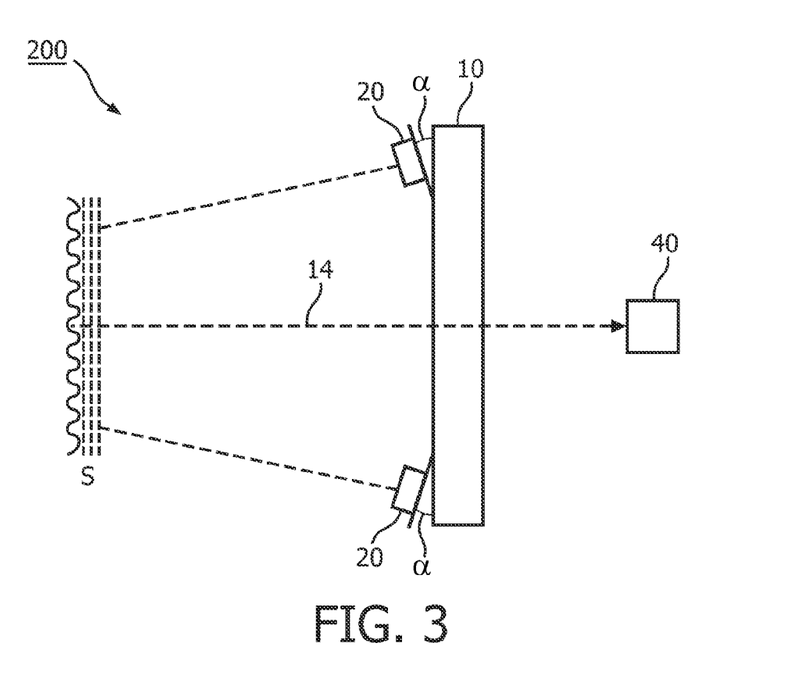
FIG. 3 is a schematic diagram of another design of an apparatus according to the teachings of the present invention.

A further benefit is that LEDs can be easily arranged on carrier 10, which can provide a uniform illumination light at the region of interest. FIG. 3 is a schematic diagram of another design of apparatus 200 according to the teachings of the present invention. As shown in FIG. 3, each LED is mounted at an angle α relative to the vertical plane of the circular board so as to achieve a desired illumination area at the region of interest. In a preferred design, the angle α for each LED may vary based on the positions of the LEDs on the circular board to provide a substantially uniform field of illumination at the region of interest.

As shown in FIG. 2, light sources equiangularly arranged on the circular board are actuated one by one in a clockwise direction. Each actuated light source provides an illumination flash to the subject. Further, two or more light sources can be actuated simultaneously to provide more illumination brightness at the region of interest.

Figure 4A:
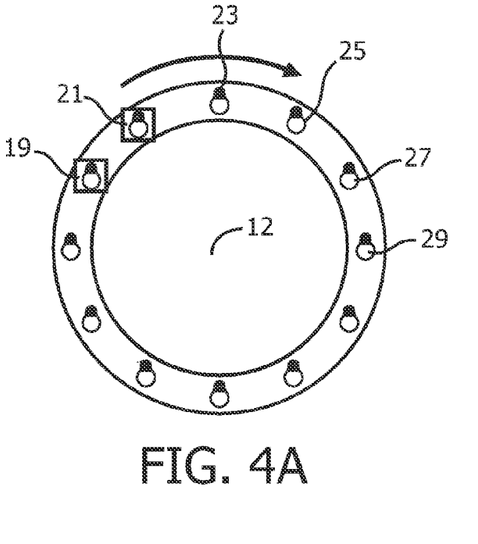
FIG. 4A and FIG. 4B are conceptual front views of light sources according to the teachings of the present invention.

FIG. 4A is a conceptual front view of light sources according to the teachings of the present invention. As shown in FIG. 4A, light sources 20 are disposed on a ring around the centre of access opening 12. The light sources are divided into groups. In one design, the light sources disposed side by side on the ring are combined into one group. For example, light source 19 and light source 21 are combined into one group. The apparatus as shown in FIG. 4A comprises six groups of light sources, each group including two light sources. The light sources in one group (e.g. light source 19 and light source 21 as the first group, light source 23 and light source 25 as the second group, light source 27 and light source 29 as the third group) are actuated simultaneously by a control of the drive currents for each group of light sources, so as to provide an illumination area with a suitable brightness at the region of interest. In one example design, a third controller is used to provide a third control signal according to the division of the light sources into groups as shown in FIG. 4A. The third control signal controls the drive circuit to supply drive currents, within a predetermined duration, to the light sources in each group simultaneously, and the drive circuit supplies drive currents to the light sources group by group in a clockwise direction. That is, within the first duration, light source 19 and light source 21 in the first group are simultaneously actuated to provide a first illumination flash to the region of the interest; within the second duration, light source 23 and light source 25 in the second group are simultaneously actuated to provide a second illumination flash to the region of the interest; within the third duration, light source 27 and light source 29 in the third group are simultaneously actuated to provide a third illumination flash to the region of the interest, and so on. As different illumination flashes are directed to the region of interest at different angles, wherein the flash duration is much shorter than the imaging period, light detector 40 can receive a mix of reflected lights originating from different groups of the light sources within the imaging period and glint can be effectively suppressed in the image that is formed based on the mix of reflected lights. The third controller may be disposed on carrier 10 or may be disposed separate from carrier 10, and the third controller is coupled to the drive circuit via a wired or wireless connection.

Figure 4B:
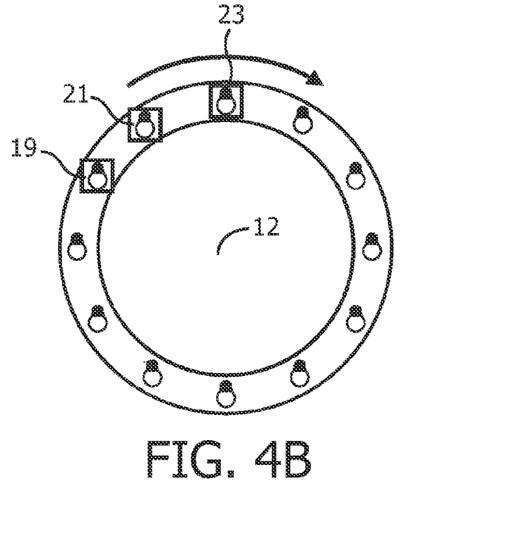

FIG. 4B is another conceptual front view of light sources according to the teachings of the present invention. As shown in FIG. 4B, light sources disposed side by side on the ring may be combined into one group, e.g. light source 19, light source 21 and light source 23. The apparatus as shown in FIG. 4B comprises four groups of light sources, each group including three light sources. The four groups of light sources are actuated group by group, and the light sources in each group (e.g. light sources 19, 21 and 23) are actuated simultaneously to provide an illumination flash with a suitable brightness at the region of interest. A fourth controller is used to provide a fourth control signal according to the division of the light sources into groups as shown FIG. 4B. The fourth control signal controls the drive circuit to supply drive currents, within a predetermined duration, to the light sources in each group simultaneously, and the drive circuit supplies drive currents to the light sources group by group in a clockwise direction.

Figure 5A:
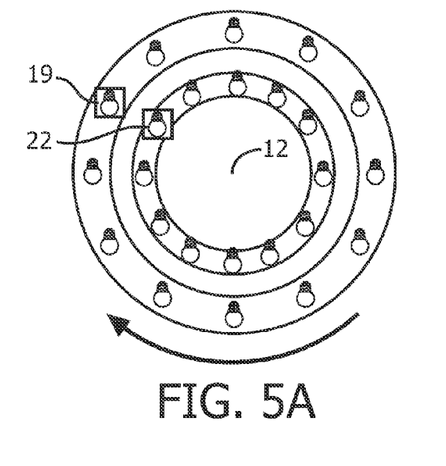
FIG. 5A, FIG. 5B and FIG. 5C are conceptual front views of light sources according to the teachings of the present invention.

FIG. 5A is another conceptual front view of light sources according to the teachings of the present invention. As shown in FIG. 5A, a plurality of light sources 20 are divided into two arrays of light sources. The two arrays of light sources are arranged on two rings around the centre of access opening 12. The light sources in the two arrays are disposed at equal tangential positions on the two rings and light sources at one equal tangential position are combined into one group, e.g. light source 19 and light source 22. The apparatus as shown in FIG. 5A comprises twelve groups of light sources, each group including two light sources. The twelve groups of light sources are actuated group by group, and the light sources in each group (e.g. a pair of light sources 19 and 22) are actuated simultaneously to provide a bright illumination flash at the region of interest. A fifth controller is used to provide a fifth control signal according to the division of the light sources into groups as shown FIG. 5A. The fifth control signal controls the drive circuit to supply drive currents, within a predetermined duration, to the light sources in each group simultaneously, and the drive circuit supplies drive currents to the light sources group by group in a clockwise direction.

Figure 5B:
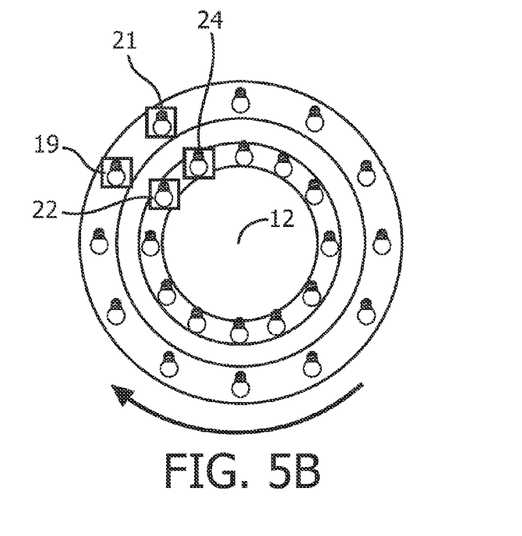

FIG. 5B is another conceptual front view of light sources according to the teachings of the present invention. As shown in FIG. 5B, a plurality of light sources 20 are divided into two arrays of light sources. The two arrays of light sources are respectively arranged on two rings around the centre of access opening 12. The light sources in the two arrays are disposed at equal tangential positions on the two rings and light sources at two equal and adjacent tangential position are combined into one groupi. For example, light source 19 and light source 22 are at an equal tangential position on the rings, and light source 21 and light source 24 are at an equal tangential position on the rings adjacent the tangential position of light source 19 and light source 22. So, these light sources, i.e. a pair of light sources 19 and 22 together with a pair of light sources 21 and 24 on the rings, are combined into one group. The apparatus as shown in FIG. 5B comprises six groups of light sources, each group including four light sources. These six groups of light sources are actuated group by group, and the light sources in each group (e.g. light sources 19, 22, 21 and 24) are actuated simultaneously to provide an illumination flash with a suitable brightness at the region of interest. A sixth controller is used to provide a sixth control signal according to the division of the light sources into groups as shown in FIG. 5B. The sixth control signal controls the drive circuit to supply drive currents, within a predetermined duration, to the light sources in each group (e.g. light sources 19, 22, 21 and 24) simultaneously, and the drive circuit supplies drive currents to the light sources group by group in a clockwise direction.

Figure 5C:
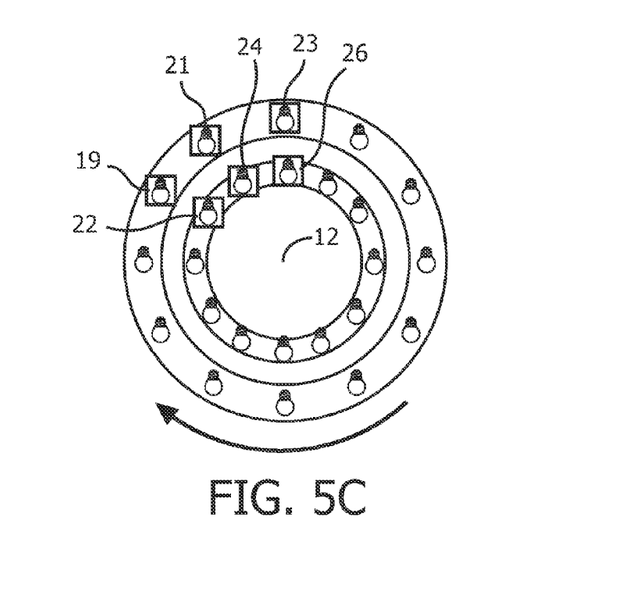

FIG. 5C is another conceptual front view of light sources according to the teachings of the present invention. Similar to the light sources in FIG. 5B, since light source 19 and light source 22, light source 21 and light source 24, light source 23 and light source 26, are correspondingly disposed at equal tangential positions on the two rings and light sources at three equal and adjacent tangential position are combined into one groupi, these light sources, i.e. a pair of light sources 19 and 22, a pair of light sources 21 and 24 together with a pair of light sources 23 and 26, are combined into one group. The apparatus as shown in FIG. 5C comprises four groups of light sources, each group including six light sources. The four groups of light sources are actuated group by group. The light sources in each group (e.g. light sources 19, 22, 21, 24, 23, 26) are actuated simultaneously to provide an illumination flash with a suitable brightness at the region of interest. A seventh controller is used to provide a seventh control signal according to the division of the light sources into groups as shown in FIG. 5C. The seventh control signal controls the drive circuit to supply drive currents, within a predetermined duration, to the light sources in each group (e.g. light sources 19, 22, 21, 24, 23, 26) simultaneously, and the drive circuit supplies drive currents to the light sources group by group in a clockwise direction.

The number of groups of light sources and the number of light sources in each group can be predetermined based on practical needs in clinical examinations. However, it is more desirable for a clinician to select or adjust the number of light sources in each group so as to provide an illumination area with a suitable brightness at the region of interest for different subjects (e.g. organs or tissue).

Figure 6:
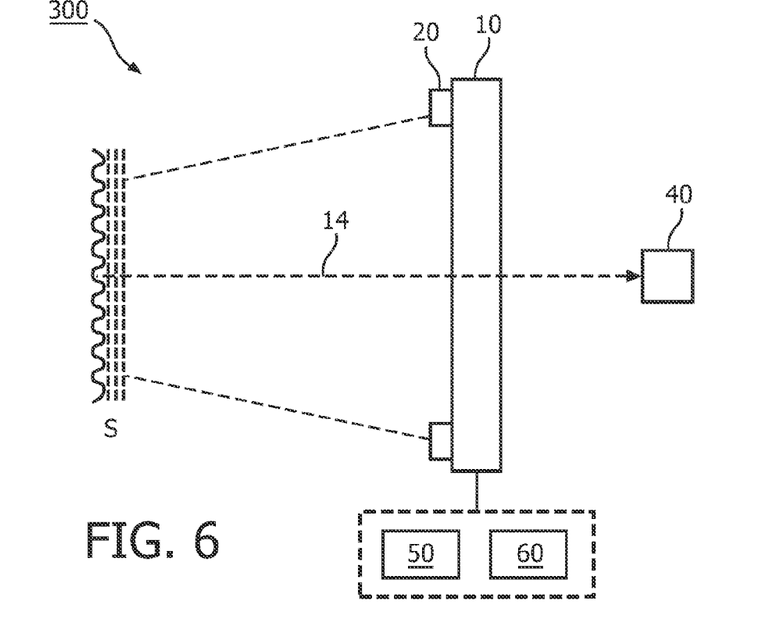
FIG. 6 is a schematic diagram of another design of an apparatus according to the teachings of the present invention.

FIG. 6 is a schematic diagram of another design of apparatus 300 according to the teachings of the present invention. The components in apparatus 300 are almost the same as those in apparatus 100 except that a controller 50 and a grouping element 60 are provided in apparatus 300.

A grouping element 60 is provided for dividing the light sources into groups. In one example design, a clinician determines a division approach, i.e. the number of groups and the number of light sources in each group, based on clinical need in a diagnostic examination (e.g. a suitable brightness illumination area at the region of interest). For example, the clinician may select one division approach from division approaches as shown in FIG. 5A, FIG. 5B and FIG. 5C and provide the selection to grouping element 60. Based on the selection, grouping element 60 sends a grouping instruction associated with the division approach to a controller 50. According to the grouping instruction, controller 50 generates an actuation control signal. In response to the actuation control signal, the driving circuit actuates the light sources correspondingly.

In one design, grouping element 60 comprises a set of buttons to be selected by the clinician, each button corresponding to one division approach. Grouping element 60 is, preferably, disposed on carrier 10 in this design. In another design, grouping element 60 provides a list of division approaches on a display from which the clinician can make a selection, and grouping element 60 is, preferably, disposed separate from carrier 10.

In another design, grouping element 60 can receive information on the division approach from a sensor. The sensor determines the number of groups and the number of light sources in each group based on, for example, a detection of the environment with respect to a region of interest for different subjects (e.g. organs or tissue).

Further, sometimes it is desirable to adjust the imaging frequency, i.e. the imaging period of the light detector. In one example design, according to the original division approach, light sources 20 are divided into twelve groups and each group includes two light sources as shown in FIG. 5A. A first adjuster (not shown) is provided to adjust the imaging period of the light detector. For example, the new imaging period is half of the original imaging period so as to increase the imaging frequency. As the imaging period is adjusted, the original division approach may have to be replaced by a new division approach, e.g. the division approach that light sources 20 are divided into six groups and each group includes four light sources as shown in FIG. 5B. Grouping element 60 sends a grouping instruction associated with the new division approach to controller 50. According to the grouping instruction, controller 50 generates an actuation control signal. In response to the actuation control signal, the driving circuit actuates the light sources correspondingly.

It is well known in photography that, once the imaging period of a light detector (e.g. exposure time of a CCD detector) is adjusted, an aperture of the CCD detector may have to be changed correspondingly to compensate for the adjustment of the exposure time of the CCD detector. Thus, a frame of image with an acceptable resolution and a suitable period can be generated accordingly. A person skilled in the art may adjust the aperture of the CCD detector to make the adjusted exposure time and the adjusted aperture of the CCD detector co-consistent. Alternatively, based on a mapping table wherein a relationship between the exposure time and the aperture of the CCD detector is provided, the adjusted exposure time and the adjusted aperture of the CCD detector can be matched with each other.

In addition, under some circumstances, it is more desirable to adjust the flash duration provided by each group of the light sources. In one example design, LEDs are used as light sources. A second adjuster (not shown) is provided to adjust the flash duration through control of the drive currents applied to the LEDs. Once the flash duration is adjusted, the division approach for dividing the light sources into groups may have to be adjusted accordingly. For example, if the flash duration is extended, the number of groups may have to be decreased in order that different groups of the light sources can provide illumination flashes at different angles to the region of interest and the light detector can receive a mix of reflected lights originating from the different groups of the light sources within the imaging period. In response to the changing of the division approach, grouping element 60 sends a grouping instruction associated with the changed division approach to controller 50. According to the grouping instruction, controller 50 generates an actuation control signal. In response to the actuation control signal, the driving circuit actuates the light sources correspondingly.

Figure 7:
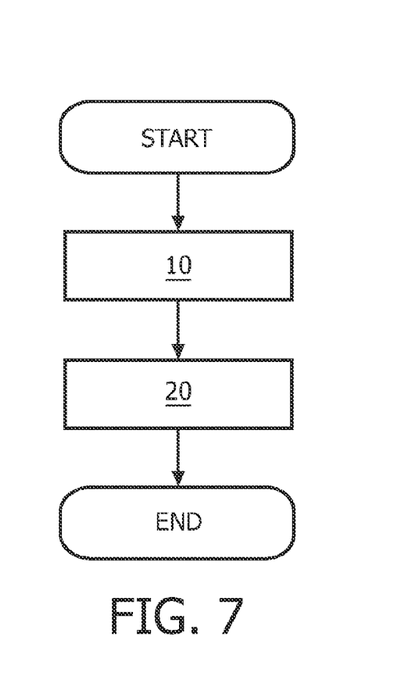
FIG. 7 is a flowchart of a process performed by the apparatus according to one design of the present invention.

FIG. 7 is a flowchart of a process performed by the apparatus according to one design of the present invention. In step S10, each group of light sources (e.g. light source 19 and light source 22 as shown in FIG. 5A) illuminates a region of interest within the subject by means of an illumination flash, wherein light sources 20 are divided into groups and these groups of light sources are actuated group by group, each actuated group of the light sources providing the illumination flash within a predetermined duration and different groups of the light sources illuminating the region of interest at different angles. In step 20, light detector 40 receives light reflected by the subject within the imaging period of light detector 40 to form a frame of image for the region of interest, wherein the duration of the illumination flash should be shorter than the imaging period so as to enable different groups of the light sources to illuminate the region of interest per imaging period.

The structure of the apparatus for imaging an object in clinical examinations should not be limited to the structures of the apparatus mentioned above. It will be apparent to those skilled in the art that the various aspects of the invention claimed may be practiced in other examples that depart from these specific details.

As described in the above designs, light sources 20 are actuated in a clockwise direction. Light sources 20 can be actuated in an anticlockwise direction also.

In addition, in an example design, light sources 20 may be actuated in sequence (e.g. light sources 15, 17, 19 . . . are actuated in succession as shown in FIG. 2); in another example design, light sources 20 may be actuated at intervals (e.g. light sources 15 and 19 . . . are alternately actuated as shown in FIG. 2).

Further, light sources 20 are arranged on two rings around the centre of the access opening 12 as shown in FIG. 5A, FIG. 5B and FIG. 5C. The light sources 20 may be arranged on more than two rings around the centre of the access opening 12. The light sources in each set correspondingly disposed in parallel on the rings may be combined into one group.

Additionally, controller 50 and grouping element 60 can be implemented using electronic hardware, computer software, or any combination thereof. Controller 50 and grouping element 60 can be separate components. Alternatively, controller 50 and grouping element 60 can be combined into one assembly, e.g. a memory plus a processor, wherein the processor implements a software program stored in the memory. Further, functions of all controllers described in the above designs may be implemented by the assembly comprised of the memory and the processor. Controller 50 can be disposed on carrier 10 or, alternatively, can be disposed separate from carrier 10. Moreover, for some light sources, a current circuit may be disposed separate from carrier 10 as well.

It should be noted that the above-mentioned solutions illustrate rather than limit the invention and that those skilled in the art will be able to design alternative solutions without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the system claims enumerating several units, several of these units can be embodied by one and the same item of software and/or hardware. The usage of the words first, second and third, et cetera, does not indicate any ordering. These words are to be interpreted as names.

The invention claimed is:

1. An apparatus for imaging a subject, comprising:
   a plurality of light sources for illuminating a region of interest within the subject, at least a portion of the light sources being divided into groups and being actuated group by group, each actuated group of the light sources providing an illumination flash within a predetermined duration, and different groups of the light sources illuminating the region of interest at different angles;
   a light detector for receiving light reflected by the subject to form a frame of image for the region of interest per imaging period of the light detector, and the duration of the illumination flash being shorter than the imaging period, enough to enable different groups of the light sources to illuminate the region of interest per imaging period;
   a controller for providing a control signal to a driving circuit for actuating the light sources according to the division of the light sources into groups; and
   a grouping element for dividing the light sources into groups.

2. The apparatus of claim 1, further comprising:
   a carrier, the light sources being arranged on the carrier to surround an access opening of the carrier, a central axis of the access opening coinciding with an optical axis for viewing the region of interest.

3. The apparatus of claim 2, wherein the light sources comprise two or more arrays of light sources, the two or more arrays of light sources being respectively arranged on two or more rings around a center of the access opening, and the light sources in the two or more arrays that are disposed in parallel on the rings are combined into one group.

4. The apparatus of claim 2, wherein the light sources disposed side by side on a ring around a center of the access opening are combined into one group.

5. The apparatus of claim 1, further comprising:
   a first adjuster for adjusting the imaging period of the light detector; and
   wherein the grouping element divides the light sources into groups based on the adjusted imaging period.

6. The apparatus of claim 5, further comprising:
   a second adjuster for adjusting the duration of the illumination flash; and
   wherein the grouping element divides the light sources into groups based on the adjusted duration of the illumination flash.

7. The apparatus of claim 1, wherein each group of the light sources is actuated once per imaging period.

8. The apparatus of claim 1, wherein the light detector is a CCD detector, and the imaging period is the exposure time of the CCD detector.

9. A method of imaging a subject, comprising:
   illuminating a region of interest within the subject by a plurality of light sources, at least a portion of the light sources being divided into groups and being actuated group by group, each actuated group of the light sources providing an illumination flash within a predetermined duration, and different groups of the light sources illuminating the region of interest at different angles;
   receiving light by a light detector to form a frame of image for the region of interest per imaging period of the light detector, the light being reflected by the subject, and the duration of the illumination flash being shorter than the imaging period, enough to enable different groups of the light sources to illuminate the region of interest per imaging period;
   providing, via a controller, a control signal to a driving circuit for actuating the light sources according to the division of the light sources into groups; and
   dividing, via a dividing element, the light sources into groups.

10. The method of claim 9, further comprising:
    adjusting the imaging period of the light detector; and
    wherein the dividing is based on the adjusted imaging period.

11. The method of claim 9, further comprising: adjusting the duration of the illumination flash; and wherein the dividing is based on the adjusted duration of the illumination flash.

* * * * *